United States Patent [19]

Deutsch et al.

[11] Patent Number: 5,384,113
[45] Date of Patent: Jan. 24, 1995

[54] STABILIZERS TO PREVENT AUTORADIOLYSIS OF RADIOLABELED PEPTIDES AND PROTEINS

[75] Inventors: Edward A. Deutsch, Maryland Heights, Mo.; Wilhelmus T. Goedemans, Bergen; Martinus T. Maria de Jong, Hoogkarspel, both of Netherlands; Kathleen M. Miller, St. Louis; James W. Brodack, Florissant, both of Mo.

[73] Assignee: Mallinckrodt Medical, Inc., St. Louis, Mo.

[21] Appl. No.: 135,882

[22] Filed: Oct. 13, 1993

Related U.S. Application Data

[63] Continuation of Ser. No. 751,825, Aug. 29, 1991, abandoned.

[51] Int. Cl.$^6$ .................. A61K 49/02; A61K 43/00
[52] U.S. Cl. .................. 424/1.69; 424/1.11; 424/1.45; 424/1.49
[58] Field of Search ............ 424/1.1, 1.11 J, 1.41, 424/1.45, 1.53, 1.69, 1.49

[56] References Cited

U.S. PATENT DOCUMENTS

| | | | |
|---|---|---|---|
| 4,229,427 | 10/1980 | Whitehouse | 424/1.1 |
| 4,232,000 | 11/1980 | Fawzi | 424/1.1 |
| 4,232,284 | 11/1980 | Fawzi | 424/1.1 |
| 4,440,738 | 4/1984 | Fawzi et al. | 424/1.1 |
| 4,497,744 | 2/1985 | Fawzi | 424/1.1 X |
| 4,504,462 | 3/1985 | Van Duzee et al. | 424/1.1 |
| 4,504,463 | 3/1985 | Van Duzee | 424/1.1 |
| 4,510,125 | 4/1985 | Grogg et al. | 424/1.1 |
| 4,707,353 | 11/1987 | Bugaj et al. | 424/1.1 |
| 4,857,299 | 8/1989 | Chia et al. | 424/1.1 |
| 4,873,074 | 10/1989 | Chia et al. | 424/1.1 |
| 5,093,105 | 3/1992 | Flanagan et al. | 424/1.1 |

FOREIGN PATENT DOCUMENTS

| | | | |
|---|---|---|---|
| 123314 | 10/1984 | European Pat. Off. | A61K 49/02 |
| 165630 | 12/1985 | European Pat. Off. | A61K 49/02 |
| WO92/00759 | 1/1992 | European Pat. Off. | A61K 43/00 |
| 2225579 | 6/1990 | United Kingdom | A61K 37/02 |
| 2239178 | 6/1991 | United Kingdom | A61K 37/43 |

OTHER PUBLICATIONS

Kwekkeboom et al., *J. Nucl. Med.*, vol. 32, No. 5, Abstract #305, p. 981 (May 1991).

Bakker et al., *J. Nucl. Med.*, vol. 31, Abstract LM10, "A Somatostatin Analogue to Image . . ." (1990).

Bakker et al., *Life Sciences*, vol. 49, "In vivo Application of [111In-DTPA-D-PHE]-Octreotide for Detection of Somatostatin Receptor Positive Tumors in Rats", pp. 1593-1601 (1991).

Bakker et al., *Life Sciences*, vol. 49, "[111In-DTPA-D-PHE]-Octreotide, A Potential Radiopharmaceutical for Imaging of Somatostatin Receptor Position Tumors; Synthesis, Radiolabeling and In Vitro Validation", pp. 1583-1591 (1991).

Billinghurst et al., *J. Nucl. Med.*, vol. 17, No. 9, "Radiation Decomposition of Technetium-99m Radiopharmaceuticals," pp. 138-143 (1979).

Tofe et al., *J. Nucl. Med.*, "In vitro Stabilization of a Low Tin Bone-Imaging Agent (99mTc-Sn-HEDP) by Ascorbic Acid," pp. 820-825 (1976).

Chemical Abstract, vol. 112, No. 21, abstract 192025n, Miholics et al. (1990).

Chemical Abstract, vol. 106, No. 3, abstract 15237p, Kishore et al. (1986).

Primary Examiner—Robert L. Stoll
Assistant Examiner—John M. Covert
Attorney, Agent, or Firm—Evan R. Witt; Brian K. Stierwalt

[57] ABSTRACT

Gentisic acid and its derivatives substantially inhibit peptide autoradiolysis. Gentisic acid or its derivatives may also be used in combination with other stabilizers such as inositol and ascorbic acid to inhibit autoradiolysis of radiolabeled peptides.

21 Claims, No Drawings

STABILIZERS TO PREVENT AUTORADIOLYSIS OF RADIOLABELED PEPTIDES AND PROTEINS

This application is a continuation of U.S. application Ser. No. 07/751,825, Aug. 29, 1991.

BACKGROUND OF THE INVENTION

This invention relates to stabilizers for radiopharmaceutical compositions. More particularly, stabilizers such as gentisic acid and its derivatives, alone or in combination with other stabilizers, are used to inhibit autoradiolysis of radiolabeled peptides and proteins.

The number of therapeutic and diagnostic uses of radiolabeled compositions is continually growing. Such uses generally involve the introduction of a suitable radiolabeled composition into a biological subject. Detection and imaging of radioactive emissions may be used to diagnose and locate the presence of aberrations, pathological conditions, and the like. In some cases, the radiolabeled composition may be designed to locate in or to seek out specific tissues or biological receptors for the purpose of delivering therapeutic radioactive emissions.

In general, a radiolabeled composition comprises a radionuclide, a carrier agent designed to target the specific organ of interest, various auxiliary agents which affix the radionuclide to the carrier, a delivery vehicle, such as water, suitable for injection into or aspiration by the patient, physiologic buffers and salts, and the like.

Some radiopharmaceutical preparations are known to require stabilizers. For example, technetium-99m and rhenium-186 compositions are unstable in oxygen and require stabilizers, such as antioxidants or reducing agents, to maintain the technetium or rhenium in a usable oxidation state. Typical reducing agents used in technetium-99m and rhenium-186 compositions include stannous, ferrous, and chromous salts. Sometimes other additives, such as ascorbic acid, d-ascorbic acid, gentisic acid, reductic acid, erythorbic acid, p-aminobenzoic acid, 4-hydroxybenzoic acid, nicotinic acid, nicotinamide, and 2,5-dihyroxy-1,4-benzenedisulfonic acid, are included to inhibit the oxidation of the radionuclide or the reducing agent.

Other radionuclides, such as $^{111}$In, $^{90}$Y, and $^{67}$Ga exist in a stable oxidation state, and therefore, do not require stabilizers to maintain their useful oxidation state.

Over the years, there has been growing interest in preparing radiolabeled proteins such as hormones, macroaggregated albumin ("MAA"), human serum albumin ("HSA"), monoclonal antibodies, or monoclonal antibody fragments for the purpose of diagnosing and treating diseases, such as inflammation, deep vein thrombosis, or cancer. In some cases, autoradiolysis of the labeled protein has been observed. To inhibit or prevent autoradiolysis, experts have suggested adding HSA to the composition (e.g., R.A.J. Kishore, et al., "Autoradiolysis of Iodinated Monoclonal Antibody Preparations," *Int J. Radiat. Appl. Instrum., Part B*, Vol. 13, No. 4, pp. 457–459 (1986)) or keeping the radiopharmaceutical composition frozen between preparation and administration (e.g., R. L. Wahl, et al., "Inhibition of Autoradiolysis of Radiolabeled Monoclonal Antibodies by Cryopreservation," *J Nuc. Med.*, Vol. 31, No. 1, pp. 84–89 (1990)). These techniques for preventing autoradiolysis are often not effective or practical when used with many radiolabeled peptides and proteins.

Recently, a number of exciting new peptides for diagnostic and therapeutic applications have been isolated and synthetically developed. One such peptide is an octapeptide somatostatin analog known as octreotide and described in U.S. Pat. No. 4,395,403. Octreotide has a very high binding affinity to somatostatin receptors in a variety of human tumors. By linking octreotide to a suitable chelating agent capable of forming a complex with radionuclides, it has been possible to create radiolabeled octreotide which effectively images tumors having somatostatin receptors. Somatostatin analogs containing chelating groups are described in UK Patent Publication No. 2,225,579.

Despite the potential usefulness of radiolabeled peptides, it has been found that they are very susceptible to autoradiolysis. As used herein, the term autoradiolysis includes chemical decomposition of the peptide by the action of radiation emitting from the radioisotope coupled to the peptide. Some believe autoradiolysis may be caused by the formation of free radicals, such as hydroxyl radicals, in the water or delivery vehicle by the radiation emitted from the radioisotope.

From the foregoing, it will be appreciated that what is needed in the art are stable radiolabeled peptide and protein compositions. Thus, it would be a significant advancement in the art to provide stabilizing agents which substantially inhibit autoradiolysis of radiolabeled peptides and proteins.

Such compositions for substantially inhibiting peptide and protein autoradiolysis are disclosed and claimed herein.

BRIEF SUMMARY OF THE INVENTION

The present invention provides compositions for preparing stable radiolabeled peptide and protein preparations. The stabilizers used in the present invention are able to substantially inhibit autoradiolysis of radiolabeled peptides and proteins. It has been found that stabilizers that are effective at preventing oxidation of radioisotopes, such as $^{99m}$Tc, are not necessarily effective at preventing autoradiolysis of peptides and proteins. Likewise, it has been found that stabilizers and techniques used to prevent autoradiolysis of proteins, such as addition of HSA or freezing, are not effective or practical in many cases. Accordingly, the present invention is directed to compositions containing stabilizers that substantially inhibit autoradiolysis of peptides and proteins.

Gentisic acid and its derivatives have been found to be very effective at inhibiting peptide and protein autoradiolysis. Gentisic acid or its derivatives may also be used in combination with other stabilizers, such as inositol and ascorbic acid, to inhibit autoradiolysis.

DETAILED DESCRIPTION OF THE INVENTION

The present invention is directed to compositions containing stabilizers that substantially inhibit autoradiolysis of peptides and proteins. One class of stabilizers that is very effective at inhibiting autoradiolysis of peptides and proteins is gentisic acid and its derivatives. The radiolabeled peptides and proteins for which the stabilizers of the present invention are needed include peptides and proteins having diagnostic and therapeutic applications.

Gentisic acid (chemically: 2,5-dihydroxybenzoic acid) is commercially available and can be prepared by several methods known in the art. Derivatives of gentisic acid include the pharmaceutically-acceptable salts and esters of gentisic acid and gentisyl alcohol. Examples of suitable gentisic acid derivatives are described in U.S. Pat. Nos. 4,497,744 and 4,232,000 which are incorporated herein by reference.

Other stabilizers such as inositol and ascorbic acid may be used in combination with gentisic acid or its derivatives to inhibit autoradiolysis of radiolabeled peptides.

The pharmaceutically-acceptable salts and esters of gentisic acid and gentisic alcohol can be prepared by standard neutralization and esterification procedures known in the art, such as the techniques described in U.S. Pat. Nos. 4,497,744 and 4,232,000. In practice, the salts and esters of gentisic acid suitable for use in the present invention can be selected according to their solubility. Soluble gentisate salts include the soluble alkali metal, alkaline earth metal, heavy metal, and ammonium salts. The alkali metal salts, such as sodium, lithium, and potassium, are very soluble and are currently preferred. The alkaline earth metal gentisate salts, such as calcium and magnesium, are less soluble, but are still suitable for use herein.

The present invention may be used with a wide range of radioisotopes capable of causing autoradiolysis of peptides. Such radioisotopes include $\gamma$-, $\beta$-, and $\alpha$-emitters.

Suitable $\gamma$-emitters include those radionuclides which are useful for diagnostic techniques. Examples of some typical $\gamma$-emitting radionuclides are $^{67}Ga$, $^{111}In$, $^{99m}Tc$, $^{169}Yb$, and $^{125}I$, $^{123}I$, and $^{201}Tl$. Examples of possible $\beta$-emitting radionuclides include those which are useful in therapeutic applications such as $^{90}Y$, $^{67}Cu$, $^{186}Re$, $^{188}Re$, $^{169}Er$, $^{121}Sn$, $^{127}Te$, $^{143}Pr$, $^{198}Au$, $^{109}Pd$, $^{165}Dy$, $^{32}P$, $^{142}Pr$, $^{177}Lu$, $^{166}Ho$, $^{153}Sm$, $^{90}Y$, $^{131}I$, $^{89}Sr$, and $^{105}Rh$. Typical $\alpha$-emitters include $^{212}Bi$, $^{211}At$, $^{241}Am$, and $^{255}Fm$.

Radiolabeling of peptides and proteins can be achieved using various methods known in the art. For example, peptides can be labeled through use of a bifunctional chelate, direct labeling, or covalent binding to a specific functional group of an amino acid side chain. The use of a bifunctional chelate involves covalent attachment of a chelate, which complexes with the radionuclide, to the peptide or protein. Possible bifunctional chelates include DTPA and $N_xS$ ligands. The DTPA may be attached to the peptide or protein by the dicyclic dianhydride method described in U.S. Pat. No. 4,479,930, which is incorporated herein by reference. $N_xS$ ligands may be attached to the peptide or protein by the methods described in U.S. Pat. No. 4,965,392 and European Patent Publication Number 0284071, which are incorporated herein by reference.

In direct labeling, the radionuclide binds to the functional group of amino acid side chains present in the peptide or protein. The radionuclide may also bind to reduced forms of a peptide or protein, such as a peptide or protein containing a reduced disulfide bond. One example of direct labeling known in the art is described in U.S. Pat. No. 4,877,868, which is incorporated by reference.

Another well known technique for labeling peptides and proteins involves covalently binding the radionuclide to one specific functional group of an amino acid side chain, such as incorporation of iodide into the phenol group of a tyrosine residue.

Commercial products for preparing radiopharmaceuticals are generally provided as lyophilized (freeze-dried) "kits" or as liquid formulations. Lyophilized kits are well known in the art. According to the present invention, lyophilized kits may contain a transfer ligand, such as citric acid, acetic acid, or sodium tartrate, a reducing agent, depending on the radioisotope that is used, a bulking agent, such as inositol or lactose, the peptide or protein to be labeled, and one or more gentisic acid stabilizers. Additional stabilizers may also be incorporated into the formulation as described herein. The radioisotope is added to the lyophilized kit just prior to patient administration.

Liquid formulations usually contain the peptide or protein labeled with the radioisotope. According to the present invention, the liquid formulation also contains one or more gentisic acid derivatives to stabilize the formulation. Other stabilizers, such as inositol and ascorbic acid, may also be included in the formulation to improve stability. A surfactant, such as polysorbate 80, and a salt solution to give a desired ionic strength, may also be added to improve stability if the solution is autoclaved. In some cases, the solution may need to be deoxygenated.

The radiolabeled compositions of the invention may be administered parenterally, preferably intravenously, in the form of injectable pharmaceutical solutions or suspensions according to conventional techniques.

Dosages employed in practicing the therapeutic method of the present invention will of course vary depending on the particular condition to be treated, for example the volume of the tumor, the particular chelate employed, the half-life of the radioisotope, and the therapy desired. In general, the dose is calculated on the basis of radioactivity distribution to each organ and on observed target uptake.

The following examples are offered to further illustrate different aspects of the present invention. These examples are intended to be purely exemplary and should not be viewed as a limitation on any claimed embodiment.

EXAMPLE 1

Preparation of $^{111}In$ labeled DTPA-octreotide with citrate additive.

To a lyophilized kit containing 10 μg DTPA-octreotide (N-[3,6,9,9-tetrakis(carboxymethyl)-3,6,9-triazanonanoyl]-D-phenylalanyl-L-hemicystyl-L-phenylalanyl-D-tryptophyl-L-lysyl-L-threonyl-L-hemicydyyl-L-threoninol cyclic (2→7) disulfide, MW=1394.60 gm/mol), 5.6 mg trisodium citrate dihydrate, and 0.4 mg citric acid monohydrate was added 1.0 ml of 0.02M HCl containing 4.70 mCi of $^{111}In$. The pH of the solution was 4.5. The solution was kept at room temperature and monitored for the amount of $^{111}In$ DTPA-octreotide using reverse-phase HPLC and a Beckman 170 radiometric detector. The HPLC method used a Hamilton PRP-1 column, 25 cm×4.1 mm, 10 microns and a gradient system, linearly ramping from 100% A (A=10:90 ethanol:water, 10 mM tetrabutyl ammonium phosphate, pH 3) to 43:57 A:B (B=50:50 ethanol:water, 10 mM tetrabutyl ammonium phosphate, pH 3) over 10 minutes, then held at 43:57 A:B for 15 minutes, then linearly ramped to 100% B over 10 minutes. The flow rate was 1.5 ml/min. The retention time of $^{111}In$ DTPA-octreotide was 30 minutes.

The purity of the $^{111}In$ labeled peptide was 87% immediately post-reconstitution and 50% at 15 hours post-reconstitution.

EXAMPLE 2

Preparation of $^{111}$In labeled DTPA-octreotide with citrate and inositol additives To a lyophilized kit containing 10 μg DTPA-octreotide (N-[3,6,9,9-tetrakis(carboxymethyl)-3,6,9-triazanonanoyl]-D-phenylalanyl-L-hemicystyl-L-phenylalanyl-D-tryptophyl-L-lysyl-L-threonyl-L-hemicydyyl-L-threoninol cyclic (2→7) disulfide, MW=1394.60 gm/mol), 5.6 mg trisodium citrate dihydrate, 0.4 mg citric acid monohydrate, and 1.0 mg inositol was added 1.0 ml of 0.02M HCl containing 6.04 mCi of $^{111}$In. The pH of the solution was 4.5. The solution was kept at room temperature and monitored for the amount of $^{111}$In DTPA-octreotide using reverse-phase HPLC and a Beckman 170 radiometric detector. The HPLC method used a Hamilton PRP-1 column, 25 cm×4.1 mm, 10 microns and a gradient system, linearly ramping from 100% A (A=10:90 ethanol:water, 10 mM tetrabutyl ammonium phosphate, pH 3) to 100% B (B=50:50 ethanol:water, 10 mM tetrabutyl ammonium phosphate, pH 3) over 60 minutes. The flow rate was 1.5 ml/min. The retention time of $^{111}$In DTPA-octreotide was 44–45 minutes.

The purity of the $^{111}$In labeled peptide was 94% immediately post-reconstitution and 73.5% at 24 hours post-reconstitution.

EXAMPLE 3

Preparation of $^{111}$In labeled DTPA-octreotide with citrate, inositol, and ascorbic acid additives To a lyophilized kit containing 10 μg DTPA-octreotide (N-[3,6,9,9-tetrakis(carboxymethyl)-3,6,9-triazanonanoyl]-D-phenylalanyl-L-hemicystyl-L-phenylalanyl-D-tryptophyl-L-lysyl-L-threonyl-L-hemicydyyl-L-threoninol cyclic (2→7) disulfide, MW=1394.60 gm/mol), 5.6 mg trisodium citrate dihydrate, and 0.4 mg citric acid monohydrate was added 1.0 mg inositol, 8.8 mg ascorbic acid, 9.9 mg sodium ascorbate, and 1.0 ml of 0.02M HCl containing 5.05 mCi of $^{111}$In. The pH of the solution was 4.0. The solution was kept at room temperature and monitored for the amount of $^{111}$In DTPA-octreotide using reverse-phase HPLC and a Beckman 170 radiometric detector. The HPLC method used a Hamilton PRP-1 column, 25 cm×4.1 mm, 10 microns and a gradient system, linearly ramping from 100% A (A=10:90 ethanol:water, 10 mM tetrabutyl ammonium phosphate, pH 3) to 100% B (B=50:50 ethanol:water, 10 mM tetrabutyl ammonium phosphate, pH 3) over 35 minutes. The flow rate was 1.5 ml/min. The retention time of $^{111}$In DTPA-octreotide was 30 minutes.

The purity of the $^{111}$In labeled peptide was 94% immediately post-reconstitution and 86% at 22 hours post-reconstitution.

EXAMPLE 4

Preparation of $^{111}$In labeled DTPA-octreotide with citrate, inositol, and gentisic acid additives To a lyophilized kit containing 10 μg DTPA-octreotide (N-[3,6,9,9-tetrakis(carboxymethyl)-3,6,9-triazanonanoyl]-D-phenylalanyl-L-hemicystyl-L-phenylalanyl-D-tryptophyl-L-lysyl-L-threonyl-L-hemicydyyl-L-threoninol cyclic (2→7) disulfide, MW=1394.60 gm/mol), 5.6 mg trisodium citrate dihydrate, and 0.4 mg citric acid monohydrate was added 1.0 mg inositol, 1.5 mg gentisic acid, and 1.0 ml of 0.02M HCl containing 5.40 mCi of $^{111}$In. The pH of the solution was 4.0. The solution was kept at room temperature and monitored for the amount of $^{111}$In DTPA-octreotide using reverse-phase HPLC and a Beckman 170 radiometric detector. The HPLC method used a Hamilton PRP-1 column, 25 cm×4.1 mm, 10 microns and a gradient system, linearly ramping from 100% A (A=10:90 ethanol:water, 10 mM tetrabutyl ammonium phosphate, pH 3) to 100% B (B=50:50 ethanol:water, 10 mM tetrabutyl ammonium phosphate, pH 3) over 60 minutes. The flow rate was 1.5 ml/min. The retention time of $^{111}$In DTPA-octreotide was 44–45 minutes.

The purity of the $^{111}$In labeled peptide was 94% immediately post-reconstitution and 94% at 48 hours post-reconstitution.

EXAMPLE 5

Preparation of $^{111}$In labeled DTPA-octreotide with gentisic acid additive

To a vial containing 10 μg DTPA-octreotide (N-[3,6,9,9-tetrakis(carboxymethyl)-3,6,9-triazanonanoyl]-D-phenylalanyl-L-hemicystyl-L-phenylalanyl-D-tryptophyl-L-lysyl-L-threonyl-L-hemicystyl-L-threoninol cyclic (2→7) disulfide, MW=1394.60 gm/mol) in 10 μl of water was added 1 ml of a degassed stock solution of 2.3 mg gentisic acid and 41.4 mg sodium gentisate dihydrate and 25 μl of 0.02M HCl containing 4.66 mCi of $^{111}$In. The pH of the solution was 4.2. The solution was kept at room temperature and monitored for the amount of $^{111}$In DTPA-octreotide using reverse-phase HPLC and a Beckman 170 radiometric detector. The HPLC method used a Hamilton PRP-1 column, 25 cm×4.1 mm, 10 microns, eluting with mobile phase A (A=20:10:70 acetonitrile:ethanol:water, 10 mM tetrabutyl ammonium phosphate, pH 3) for 9 minutes, then eluting with mobile phase B (B=50:10:40 acetonitrile:ethanol:water, 10 mM tetrabutyl ammonium phosphate, pH 3) from 9 to 15 minutes. The flow rate was 1.2 ml/min. The retention time of $^{111}$In DTPA-octreotide was 9–10 minutes.

The purity of the $^{111}$In labeled peptide was 97% immediately post-reconstitution and 97% at 72 hours post-reconstitution.

EXAMPLE 6

Preparation of $^{111}$In labeled DTPA-octreotide with acetate and nicotinic acid additives To a lyophilized kit containing 10 μg DTPA-octreotide (N-[3,6,9,9-tetrakis(carboxymethyl)-3,6,9-triazanonanoyl]-D-phenylalanyl-L-hemicystyl-L-phenylalanyl-D-tryptophyl-L-lysyl-L-threonyl-L-hemicystyl-L-threoninol cyclic (2→7) disulfide, MW=1394.60 gm/mol) and acetate buffer, pH 4, was added 12.3 mg nicotinic acid and 1.0 ml of 0.02M HCl containing 2.45 mCi of $^{111}$In. The pH of the solution was 3.8. The solution was kept at room temperature and monitored for the amount of $^{111}$In DTPA-octreotide using reverse-phase HPLC and a Beckman 170 radiometric detector. The HPLC method used a Hamilton PRP-1 column, 25 cm×4.1 mm, 10 microns and a gradient system, linearly ramping from 100% A (A=10:90 ethanol:water, 10 mM tetrabutyl ammonium phosphate, pH 3) to 100% B (B=50:50 ethanol:water, 10 mM tetrabutyl ammonium phosphate, pH 3) over 60 minutes. The flow rate was 1.5 ml/min. The retention time of $^{111}$In DTPA-octreotide was 44–45 minutes.

The purity of the $^{111}$In labeled peptide was 90% immediately post-reconstitution and 80% at 24 hours post-reconstitution.

EXAMPLE 7

Preparation of $^{111}$In labeled DTPA-octreotide with citrate, inositol and resorcinol additives To a lyophilized kit containing 10 μg DTPA-octreotide (N-[3,6,9,9-tetrakis(carboxymethyl)-3,6,9-triazanonanoyl]-D-Phenylalanyl-L-hemicystyl-L-phenylalanyl-D-tryptophyl-L-lysyl-L-threonyl-L-hemicystyl-L-threoninol cyclic (2→7) disulfide, MW=1394.60 gm/mol), 5.6 mg trisodium citrate dihydrate, and 0.4 mg citric acid monohydrate was added 1.0 mg inositol, 11 mg resorcinol, and 1.0 ml of 0.02M HCl containing 5.17 mCi of $^{111}$In. The pH of the solution was 4.5. The solution was kept at room temperature and monitored for the amount of $^{111}$In DTPA-octreotide using reverse-phase HPLC and a Beckman 170 radiometric detector. The HPLC method used a Hamilton PRP-1 column, 25 cm×4.1 mm, 10 microns and a gradient system, linearly ramping from 100% A (A=10:90 ethanol:water, 10 mM tetrabutyl ammonium phosphate, pH 3) to 43:57 A:B (B=50:50 ethanol:water, 10 mM tetrabutyl ammonium phosphate, pH 3) over 10 minutes, then held at 43:57 A:B for 15 minutes, then linearly ramped to 100% B over 10 minutes. The flow rate was 1.5 ml/min. The retention time of $^{111}$In DTPA-octreotide was 30 minutes.

The purity of the $^{111}$In labeled peptide was 81% immediately post-reconstitution (also, 6% of an $^{111}$In transfer ligand complex) and 87% at 120 hours post-reconstitution.

The results of Examples 1–7 are summarized in Table 1. These results demonstrate that gentisic acid, either alone or in combination with other stabilizers, is very effective at preventing radiolysis of radiolabeled peptides.

TABLE 1

| Example | Additive(s) | Initial Purity | Stability |
|---|---|---|---|
| 1 | citrate | 87% | 50% @ 15 hrs |
| 2 | citrate inositol | 94% | 73.5% @ 24 hrs |
| 3 | citrate inositol ascorbic acid | 94% | 86% @ 22 hrs |
| 4 | citrate inositol gentisic acid | 94% | 94% @ 48 hrs |
| 5 | gentisic acid | 97% | 97% @ 72 hrs |
| 6 | acetate nicotinic acid | 90% | 80% @ 24 hrs |
| 7 | inositol resorcinol | 87%* | 87% @ 120 hrs |

*81% $^{111}$In DTPA-octreotide and 6% transfer ligand complex.

EXAMPLE 8

Preparation of $^{123}$I labeled LH-RH

This preparation is done in a well-ventilated fume hood equipped with a charcoal filter to absorb any volatile iodine.

In a 1.5 ml polyethylene tube, add 70 μl of buffer A (A=150 mM sodium phosphate, pH 7.4), 10 μl of a 0.1 mM solution of LH-RH (des-gly$^{10}$, [D-ala$^6$]-LH-RH ethylamide) in 0.1M acetic acid, and 5 mCi of $^{123}$I in 5 μl of 0.01M NaOH. The reaction is started by adding 10 μl of a chloramine T solution (0.5 mg chloramine T/ml buffer A) to the peptide solution and is mixed by cautious aspiration and expulsion of the reaction mixture with the pipet used to add chloramine T. After 1 minute, 100 μl of sodium metabisulfite solution (1 mg sodium metabisulfite/ml buffer A) is added to terminate the reaction and the reaction is mixed with the pipet as explained previously. The reaction is kept in the hood a few minutes to allow any volatile iodine to exhaust from the reaction vial into the hood.

The solution is loaded onto a PD-10 column (G-25M Sephadex PD-10 column; Pharmacia LKB Biotechnology Inc.; Piscataway, N.J.) eluting with PBS, pH 7.4, and 0.5 ml fractions are collected. The $^{123}$I labeled LH-RH is in fractions 6 and 7, which are subsequently combined. Half of this solution is transferred to another vial containing 2 mg of gentisic acid.

The $^{123}$I LH-RH solutions are kept at room temperature and monitored for the amount of iodinated peptide and the amount of free iodide using reverse-phase HPLC and a Beckman 170 radiometric detector. The HPLC method uses a Hamilton PRP-3 column, 15 cm×4.1 mm, 10 microns and a gradient system eluting from 100% A (A=15:85 acetonitrile:water, 6 mM HCl) to 100% B (B=50:50 acetonitrile:water, 6 mM HCl) over 30 minutes. Free iodide elutes at the void volume in this system while the $^{123}$I LH-RH is retained and has a longer retention time. The solution containing the radiolabeled peptide without the gentisic acid stabilizer shows evidence of autoradiolytic degradation by the appearance of an increasing amount of free iodide in solution, as determined by HPLC analysis.

EXAMPLE 9

Preparation of $^{186}$Re labeled N$_3$S-NR-Lu-10

The NR-Lu-10 monoclonal antibody (NeoRx Corporation, Seattle, Wash.) is labeled with $^{186}$Re using the pre-formed chelate approach developed by NeoRx and described in U.S. Pat. No. 4,965,392 and European Patent Publication Number 0284071. The ligand used to form the $^{186}$Re complex is a tetrafluorophenyl ester of [N-(S-ethoxyethyl mercapto)acetylamino)adipoyl-glycyl]glycine. The $^{186}$Re complex formed is referred to as a $^{186}$Re-N$_3$S complex, since the $^{186}$Re is coordinated by the three nitrogens and the one sulfur atom of the ligand. The $^{186}$Re complex is formed by reducing 0.5 ml of $^{186}$Re perrhenate (400 mCi, 4 mCi/μg Re) contained in a purged 10 ml vial with 0.5 ml of a deoxygenated stock solution of 1 mg stannous chloride, 10 mg gentisic acid, and 250 mg citric acid. The solution is kept at room temperature for 15 minutes. To this solution is added 0.2 ml of a 1 mg ligand/1 ml isopropanol stock solution. The solution is heated for 15 minutes at 80° C.

A solution of 25 mg of protein in 1.0 ml PBS is added to the vial containing the $^{186}$Re-N$_3$S complex. The pH of the solution is adjusted to pH 9–9.5 with a 0.2M sodium carbonate buffer. The solution is incubated at room temperature for 15 minutes. Given a typical conjugation yield of 50%, this reaction yields $^{186}$Re-N$_3$S-NR-Lu-10 at a specific activity of 200 mCi $^{186}$Re/25 mg NR-Lu-10.

The $^{186}$Re-N$_3$S-NR-Lu-10 is purified using a PD-10 column (G-25M Sephadex PD-10 column; Pharmacia LKB Biotechnology Inc.; Piscataway, N.J.) eluting with PBS, pH 7.4, collecting 0.5 ml fractions. The $^{186}$Re-N$_3$S-NR-Lu-10 elutes in fractions 6 and 7, which are subsequently combined. Half of this solution is transferred to a vial containing 10 mg of gentisic acid.

The labeled protein is kept at room temperature and is monitored for the purity of $^{186}$Re-N$_3$S-NR-Lu-10 using HPLC with a gel permeation column (Zorbax GF-250; 9.4 mm×25.0 cm; DuPont, Wilmington, Del.) eluting with 0.1M phosphate, 0.1% sodium dodecyl sulfate, pH 6.7 mobile phase at a flow rate of 1 ml/min. Presence of autoradiolytic decomposition of the labeled monoclonal antibody is detected by the appearance of HPLC peaks that do not correspond to that for the $^{186}$Re-N$_3$S-NR-Lu-10 monoclonal antibody. The radiolytic decomposition occurs in the solution that does not contain gentisic acid.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of preventing autoradiolysis of radiolabeled peptides by including a stabilizer selected from the group consisting of gentisic acid, genetisyl alcohol and water soluble salts, esters, and mixtures thereof in a pharmaceutically acceptable carrier containing a biologically active peptide radiolabeled with a radionuclide selected from the group consisting of $^{111}$In, $^{67}$Ga, $^{169}$Yb, $^{125}$I, $^{123}$I, and $^{201}$Tl, wherein said stabilizer is present in an amount effective to prevent autoradiolysis of the radiolabeled biologically active peptide.

2. A method of preventing autoradiolysis of radiolabeled peptides as defined in claim 1, wherein the radiolabeled biologically active peptide is labeled with a radionuclide by use of a bifunctional chelate.

3. A method of preventing autoradiolysis of radiolabeled peptides as defined in claim 1, wherein the radiolabeled biologically active peptide is labeled with a radionuclide by direct labeling of the peptide.

4. A method of preventing autoradiolysis of radiolabeled peptides as defined in claim 1, wherein the pharmaceutically acceptable carrier further comprises a second stabilizer.

5. A method of preventing autoradiolysis of radiolabeled peptides as defined in claim 4, wherein the second stabilizer includes inositol.

6. A method of preventing autoradiolysis of radiolabeled peptides as defined in claim 4, wherein the second stabilizer includes ascorbic acid.

7. A method of preventing autoradiolysis of radiolabeled peptides as defined in claim 1, wherein the pharmaceutically acceptable carrier contains a buffer.

8. A method of preventing autoradiolysis of radiolabeled peptides as defined in claim 1, wherein the radionuclide is $^{111}$In.

9. A method of preventing autoradiolysis of radiolabeled peptides as defined in claim 8, wherein the peptide is octreotide.

10. A method of preventing autoradiolysis of radiolabeled proteins by including a stabilizer selected from the group consisting of gentisic acid, gentisyl alcohol and water soluble salts, esters, and mixtures thereof in a pharmaceutically acceptable carrier containing a biologically active protein radiolabeled with a radionuclide selected from the group consisting of $^{111}$In, $^{67}$Ga, $^{169}$Yb, $^{125}$I, $^{123}$I, and $^{201}$Tl, wherein said stabilizer is present in an amount effective to prevent autoradiolysis of the radiolabeled biologically active protein.

11. A method of preventing autoradiolysis of radiolabeled proteins as defined in claim 10, wherein the radiolabeled biologically active protein is labeled with a radionuclide by use of a bifunctional chelate.

12. A method of preventing autoradiolysis of radiolabeled proteins as defined in claim 10, wherein the radiolabeled biologically active protein is labeled with a radionuclide by direct labeling of the protein.

13. A method of preventing autoradiolysis of radiolabeled proteins as defined in claim 10, wherein the pharmaceutically acceptable carrier contains a buffer.

14. A method of preventing autoradiolysis of radiolabeled proteins as defined in claim 10, wherein the radionuclide is $^{111}$In.

15. A composition for preparing a radiolabeled octreotide preparation stable to autoradiolysis comprising:
   a quantity of DTPA-octreotide, wherein the DTPA-octreotide is labeled with $^{111}$In; and
   a stabilizer selected from the group consisting of gentisic acid, gentisyl alcohol, and the water soluble salts, esters, derivatives, and mixtures thereof.

16. A composition as defined in claim 15, further comprising a second stabilizer.

17. A composition as defined in claim 16, wherein the second stabilizer includes inositol.

18. A composition as defined in claim 16, wherein the second stabilizer includes ascorbic acid.

19. A composition as defined in claim 16, further comprising a buffer.

20. A composition as defined in claim 19, wherein the composition is in the form of a lyophilized kit.

21. A composition as defined in claim 15, wherein the composition is a liquid formulation.

* * * * *